(12) United States Patent
Christensen, IV

(10) Patent No.: US 6,518,306 B1
(45) Date of Patent: Feb. 11, 2003

(54) 1,4-SUBSTITUED 4,4-DIARYL CYCLOHEXANES

(75) Inventor: Siegfried B. Christensen, IV, Philadelphia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/031,927

(22) PCT Filed: Aug. 10, 2000

(86) PCT No.: PCT/US00/21867
§ 371 (c)(1),
(2), (4) Date: Jan. 24, 2002

(87) PCT Pub. No.: WO01/10385
PCT Pub. Date: Feb. 15, 2001

Related U.S. Application Data

(60) Provisional application No. 60/148,034, filed on Aug. 10, 1999.

(51) Int. Cl.[7] .......................... A01N 37/00; C07C 69/76
(52) U.S. Cl. .......................... 514/532; 560/51; 560/59; 560/102; 504/172; 568/659
(58) Field of Search .......................... 560/59, 102, 51; 564/169, 172; 568/659; 514/532

(56) References Cited

FOREIGN PATENT DOCUMENTS

WO          407278038          8/1998

*Primary Examiner*—Paul J. Killos
(74) *Attorney, Agent, or Firm*—James M. Kanagy; Charles M. Kinzig

(57) ABSTRACT

This invention relates to compounds of Formula (I) where Z is an amine, alcohol or derivative thereof, and the ketone analog thereof.

11 Claims, No Drawings

1,4-SUBSTITUTED 4,4-DIARYL CYCLOHEXANES

This application is a 371 of PCT/US00/21867 filed Aug. 10, 2000 which claims benefit of Provisional Serial No. 60/148,034 filed Aug. 10, 1999.

AREA OF THE INVENTION

This invention relates to compounds which are PDE4 inhibitors particularly in regards to treating allergic and inflammatory diseases and for inhibiting the production of Tumor Necrosis Factor (TNF). They are particularly use for treating pulmonary diseases such as various forms of asthma and chronic obstructive pulmonary disease.

BACKGROUND OF THE INVENTION

The compounds of this invention can be used in treating conditions which are modulated by the inhibition of PDE4. They have particular application in regards to treating allergic and inflammatory diseases and for inhibiting the production of Tumor Necrosis Factor (TNF).

As regards anti-inflammatory activity, one target disease is chronic obstructive pulmonary disease (COPD). COPD is an umbrella term frequently used to describe two conditions of fixed airways disease, chronic bronchitis and emphysema. Chronic bronchitis and emphysema are most commonly caused by smoking; approximately 90% of patients with COPD are or were smokers. Approximately 50% of smokers develop chronic bronchitis, and about 15% of smokers develop disabling airflow obstruction. The airflow obstruction associated with COPD is progressive, may be accompanied by airway hyperactivity, and may be partially reversible. Non-specific airway hyper-responsiveness may also play a role in the development of COPD and may be predictive of an accelerated rate of decline in lung function in smokers.

Another disease treatable with PDE4 inhibitors is asthma, particularly asthma caused by extrinsic stimuli. It is a complex, multifactorial disease characterized by reversible narrowing of the airway and hyperactivity of the respiratory tract to external stimuli. Multiple mediators are responsible for the development of asthma. It seems unlikely that eliminating the effects of a single mediator will have a substantial effect on all three components of chronic asthma. An alternative to the "mediator approach" is to regulate the activity of the cells responsible for the pathophysiology of the disease. One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE 4, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd, 1989]. Research indicates that inhibition of this enzyme not only produces airway smooth muscle relaxation, but also suppresses degranulation of mast cells. basophils and neutrophils along with inhibiting the activation of monocytes and neutrophils. Moreover, the beneficial effects of PDE 4 inhibitors are markedly potentiated when adenylate cyclase activity of target cells is elevated by appropriate hormones or autocoids, as would be the case in vivo. Thus PDE 4 inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of tumor necrosis factor (TNF), a serum glycoprotein. Excessive or unregulated TNF production has been implicated in mediating or exacerbating a number of diseases including rheumatoid arthritis, rheumatoid spondylitis. osteoarthritis, gouty arthritis and other arthritic conditions: sepsis. septic shock. endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), ARC (AIDS related complex). keloid formation, scar tissue formation, Crohn's disease, ulcerative colitis, or pyresis, in addition to a number of autoimmune diseases, such as multiple sclerosis, auto-immune diabetes and systemic lupus erythematosis.

This invention provides compound which are useful in treating these diseases, and others modulated by PDE4, by inhibiting one or more of the various isoforms of PDE4.

SUMMARY OF THE INVENTION

In a first aspect this invention relates to a compound of Formula(I)

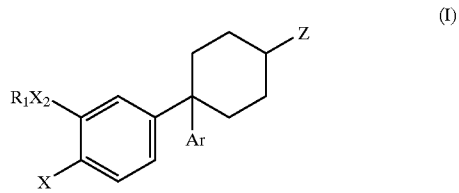

(I)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties unsubstituted or substituted with one or more halogens;
m is 0 to 2;
n is 1 to 4;

r is 0 to 6;

$R_4$ and $R_5$ are independently selected hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;

provided that:
- a) when $R_6$ is hydroxyl, then m is 2; or
- b) when $R_6$ is hydroxyl, then r is 2 to 6; or
- c) when $R_6$ is 2-tetrahydropyranyl, 2-tetrahydrothiopyranyl, 2-tetrahydrofuranyl, or 2-tetrahydrothienyl, then m is 1 or 2; or
- d) when $R_6$ is 2-tetrahydropyranyl, 2-tetrahydrothiopyranyl, 2-tetrahydrofuranyl, or 2-tetrahydrothienyl, then r is 1 to 6;
- e) when n is 1 and m is 0, then $R_6$ is other than H in $-(CR_4R_5)_nO(CR_4R_5)_mR_6$;

X is $YR_2$, fluorine, $NR_4R_5$, or formyl amine;

Y is O or $S(O)_{m'}$, m' is 0, 1, or 2;

$X_2$ is O or $NR_8$;

$X_4$ is H, $R_9$, $OR_8$, CN, $C(O)R_8$, $C(O)OR_8$, $C(O)NR_8R_8$, or $NR_8R_8$;

$R_2$ is independently selected from $-CH_3$ or $-CH_2CH_3$ optionally substituted by 1 or more halogens;

s is 0 to 4;

Ar is phenyl unsubstituted or substituted by $R_7$;

Z is $OR_{14}$, $OR_{15}$, $SR_{14}$, $S(O)_mR_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

Y' is O or S;

$R_7$ is $-(CR_4R_5)_qR_{12}$ or $C_{1-6}$ alkyl wherein: the $R_{12}$ or $C_{1-6}$ alkyl group is unsubstituted or substituted one or more times by methyl or ethyl unsubstituted or substituted by 1–3 fluorines; $-F$; $-Br$; $-Cl$; $-NO_2$; $-NR_{10}R_{11}$; $-C(O)R_8$; $-CO_2R_8$; $-O(CH_2)_{2-4}OR_8$; $-O(CH_2)_qR_8$; $-CN$; $-C(O)NR_{10}R_{11}$; $-O(CH_2)_qC(O)NR_{10}R_{11}$; $-O(CH_2)_qC(O)R_9$; $-NR_{10}C(O)NR_{10}R_{11}$; $-NR_{10}C(O)R_{11}$; $-NR_{10}C(O)OR_9$; $-NR_{10}C(O)R_{13}$; $-C(NR_{10})NR_{10}R_{11}$; $-C(NCN)NR_{10}R_{11}$; $-C(NCN)SR_9$; $-NR_{10}C(NCN)SR_9$; $-NR_{10}C(NCN)NR_{10}R_{11}$; $-NR_{10}S(O)_2R_9$; $-S(O)_mR_9$; $-NR_{10}C(O)C(O)NR_{10}R_{11}$; $-NR_{10}C(O)C(O)R_{10}$; or $R_{13}$;

q is 0, 1, or 2;

$R_{12}$ is $R_{13}$, $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$; or $C_3$–$C_7$ cycloalkyl, or (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, or phenyl, wherein each of (2-, 3- or 4-pyridyl), pyrimidinyl, pyrazolyl, (1-or 2-imidazolyl), pyrrolyl, piperazinyl, piperidinyl, morpholinyl, furanyl, (2- or 3-thienyl), quinolinyl, naphthyl, or phenyl may be substituted by $OR_{14}$, $OR_{15}$, $SR_{14}$, $S(O)_mR_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_qNR_8R_{14}$ or $S(O)_qR_7$ where q is 0, 1 or 2;

provided that:
- (f) $R_7$ is not $C_{1-4}$ alkyl unsubstituted or substituted by one to three fluorines;

or the pharmaceutically acceptable salts thereof.

In addition this invention covers the 1-position ketones analogous to Formula (I), namely compounds of Formula (II)

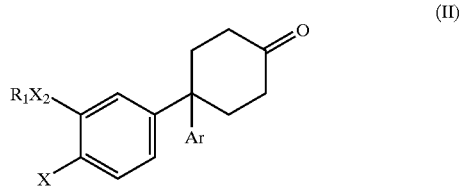

(II)

wherein the various groups on Formula (II) other than Z are the same as for Formula (I).

DETAILED DESCRIPTION OF THE INVENTION

This invention relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I) and (II).

Phosphodiesterase 4 inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE 4 inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) and (II) The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) and (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole: the class of compounds called the triazoles, such as fluconazole, and itranazole, and the class of compound called the Amphotericins, in particular Amphotericin B and liposomal Amphotericin B.

The compounds of Formula (I) may also be used for inhibiting and/or reducing the toxicity of an anti-fungal, anti-bacterial or anti-viral agent by administering an effective amount of a compound of Formula (I) and (II) to a mammal in need of such treatment. Preferably, a compound of Formula (I) and (II) is administered for inhibiting or reducing the toxicity of the Amphotericin class of compounds, in particular Amphotericin B.

"Inhibiting the production of IL-1" or "inhibiting the production of INF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-$\beta$ (also known as lymphotoxin) has close structural homology with TNF-$\alpha$ (also known as cachectin), and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise. Preferably TNF-$\alpha$ is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, this cytokine is TNF-$\alpha$.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. The parent compound, dissolved in a suitable solvent, is treated with an excess of an organic or inorganic acid, in the case of acid addition salts of a base, or an excess of organic or inorganic base where the molecule contains a COOH for example.

Pharmaceutical compositions of the present invention comprise a pharmaceutical carrier or diluent and some amount of a compound of the Formula (I) and (II). The compound may be present in an amount to effect a physiological response, or it may be present in a lesser amount such that the user will need to take two or more units of the composition to effect the treatment intended. These compositions may be made up as a solid, liquid or in a gaseous form. Or one of these three forms may be transformed to another at the time of being administered such as when a solid is delivered by aerosol means, or when a liquid is delivered as a spray or aerosol.

The nature of the composition and the pharmaceutical carrier or diluent will of course, depend upon the intended route of administration, for example parenterally, topically, orally or by inhalation.

For topical administration the pharmaceutical composition will be in the form of a cream, ointment, liniment, lotion, pastes, aerosols, and drops suitable for administration to the skin, eye, ear, or nose.

For parenteral administration the pharmaceutical composition will be in the form of a sterile injectable liquid such as an ampule or an aqueous or non-aqueous liquid suspension.

For oral administration the pharmaceutical composition will be in the form of a tablet, capsule, powder, pellet, atroche, lozenge, syrup, liquid, or emulsion.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The pharmaceutical preparations thus described are made following the conventional techniques of the pharmaceutical chemist as appropriate to the desired end product.

In these compositions, the amount of carrier or diluent will vary but preferably will be the major proportion of a suspension or solution of the active ingredient. When the diluent is a solid it may be present in lesser, equal or greater amounts than the solid active ingredient.

Usually a compound of Formula I is administered to a subject in a composition comprising a nontoxic amount sufficient to produce an inhibition of the symptoms of a disease in which leukotrienes are a factor. Topical formulations will contain between about 0.01 to 5.0% by weight of the active ingredient and will be applied as required as a preventative or curative agent to the affected area. When employed as an oral, or other ingested or injected regimen, the dosage of the composition is selected from the range of from 1 mg to 1000 mg of active ingredient for each administration. For convenience, equal doses will be administered 1 to 5 times daily with the daily dosage regimen being selected from about 1 mg to about 5000 mg.

Preferred compounds of either Formula (I) or (II) are as follows:

When $R_1$ is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) are $CH_2$-cyclopropyl, $CH_2$-$C_{5-6}$ cycloalkyl, $C_{4-6}$ cycloalkyl unsubstituted or substituted with OH, $C_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O$-$(CH_2)_{0-2}CH_3$, —$(CH_2)_{1-3}O(CH_2)_{0-2}CH_3$, and —$(CH_2)_{2-4}$OH.

When $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH$(—$CH_3$)—, for instance. The individual hydrogen atoms of the repeating methylene unit or the branching hydrocarbon can unsubstituted or be substituted by fluorine independent of each other to yield, for instance, the preferred $R_1$ substitutions, as noted above. When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987.

Z is preferably $OR_{14}$, $OR_{15}$, $SR_{14}$, $S(O)_m R_7$, $S(O)_2 NR_{10}R_{14}$, $NR_{10}R_{14}$, $NR_{14}C(O)R_9$, $NR_{10}C(O)R_{14}$, $NR_{10}C(O)OR_7$, $NR_{10}C(O)NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$.

Preferred X groups for Formula (I) are those wherein X is $YR_2$ and Y is oxygen. The preferred $X_2$ group for Formula (I) is that wherein $X_2$ is oxygen. Preferred $R_2$ groups, where applicable, is a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_7$ moieties include unsubstituted or substituted —$(CH_2)_{1-2}$(cyclopropyl), —$(CH_2)_{0-2}$(cyclobutyl), —$(CH_2)_{0-2}$(cyclopentyl) unsubstituted or substituted by OH, —$(CH_2)_{0-2}$(cyclohexyl), —$(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), and $(CH_2)_{0-2}$phenyl.

Preferred rings when $R_{10}$ and $R_{11}$ in the moiety —$NR_{10}R_{11}$ together with the nitrogen to which they are attached form a 5 to 7 membered ring comprised of carbon or carbon and at least one heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring comprised of carbon or carbon and at least one heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but is not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, 4-($R_{14}$)-1-piperazinyl, or 4-($R_{15}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the $R_7$ group is unsubstituted or substituted by a heterocyclic ring such as imidazolyl, pyrazolyl, triazolyl, tetrazolyl, or thiazolyl, the heterocyclic ring itself may be unsubstituted or substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

Preferred are those compounds of Formula (I) wherein $R_1$ is —$CH_2$-cyclopropyl, —$CH_2$—$C_{5-6}$ cycloalkyl, —$C_{4-6}$ cycloalkyl unsubstituted or substituted by OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, and X is $YR_2$.

Most preferred are those compounds wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl.

The most perferred compounds are:
4-[4-(2-aminopyrimidin-5-yl)phenyl]-4-(3-cyclopentyl-oxy-4-methoxyphenyl)-cyclohexanone;
cis-4-[4-(2-aminopyrimidin-5-yl)phenyl]-4-(3-cyclo-pentyloxy-4-methoxyphenyl)-cyclohexanol;
trans-4-[4-(2-aminopyrimidin-5-yl)phenyl]-4-(3-cyclo-pentyloxy-4-methoxyphenyl)-cyclohexyl-1-amine;
cis-4-[4-(2-Aminopyrimidin-5-yl)phenyl]-4-(3-cyclo-pentyloxy-4-methoxyphenyl)-cyclohexyl-1-amine; and
trans-4-[4-(2-Aminopyrimidin-5-yl)phenyl]-4-(3-cyclo-pentyloxy-4-methoxyphenyl)-cyclohexyl-1-amine.

The following examples are given to further illustrate the described invention. These examples are intended solely for illustrating the invention and should not be read to limit the invention in any manner. Reference is made to the claims for what is reserved to the inventors hereunder.

No unacceptable toxicological effects are expected when these compounds are administered in accordance with the present invention.

Compounds of the Formula I can be prepared by methods described in Scheme 1.

Scheme 1

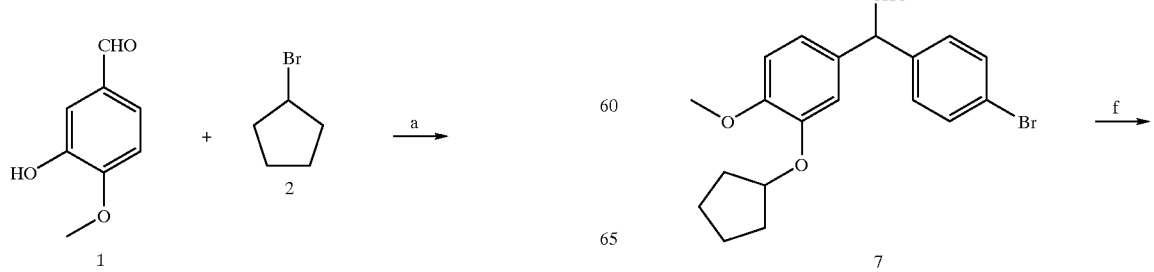

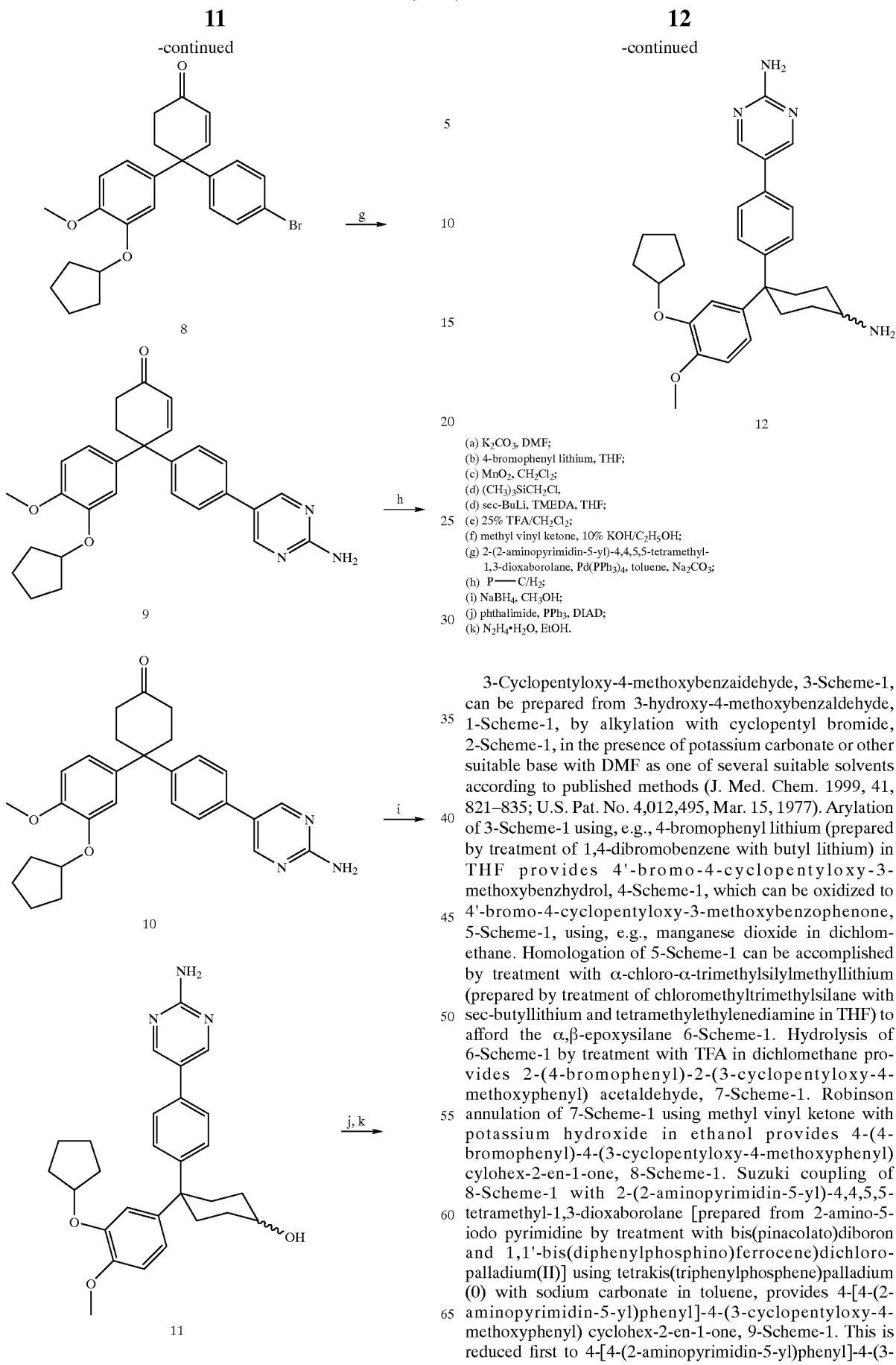

(a) K$_2$CO$_3$, DMF;
(b) 4-bromophenyl lithium, THF;
(c) MnO$_2$, CH$_2$Cl$_2$;
(d) (CH$_3$)$_3$SiCH$_2$Cl,
(d) sec-BuLi, TMEDA, THF;
(e) 25% TFA/CH$_2$Cl$_2$;
(f) methyl vinyl ketone, 10% KOH/C$_2$H$_5$OH;
(g) 2-(2-aminopyrimidin-5-yl)-4,4,5,5-tetramethyl-1,3-dioxaborolane, Pd(PPh$_3$)$_4$, toluene, Na$_2$CO$_3$;
(h) P—C/H$_2$;
(i) NaBH$_4$, CH$_3$OH;
(j) phthalimide, PPh$_3$, DIAD;
(k) N$_2$H$_4$·H$_2$O, EtOH.

3-Cyclopentyloxy-4-methoxybenzaldehyde, 3-Scheme-1, can be prepared from 3-hydroxy-4-methoxybenzaldehyde, 1-Scheme-1, by alkylation with cyclopentyl bromide, 2-Scheme-1, in the presence of potassium carbonate or other suitable base with DMF as one of several suitable solvents according to published methods (J. Med. Chem. 1999, 41, 821–835; U.S. Pat. No. 4,012,495, Mar. 15, 1977). Arylation of 3-Scheme-1 using, e.g., 4-bromophenyl lithium (prepared by treatment of 1,4-dibromobenzene with butyl lithium) in THF provides 4'-bromo-4-cyclopentyloxy-3-methoxybenzhydrol, 4-Scheme-1, which can be oxidized to 4'-bromo-4-cyclopentyloxy-3-methoxybenzophenone, 5-Scheme-1, using, e.g., manganese dioxide in dichlomethane. Homologation of 5-Scheme-1 can be accomplished by treatment with α-chloro-α-trimethylsilylmethyllithium (prepared by treatment of chloromethyltrimethylsilane with sec-butyllithium and tetramethylethylenediamine in THF) to afford the α,β-epoxysilane 6-Scheme-1. Hydrolysis of 6-Scheme-1 by treatment with TFA in dichlomethane provides 2-(4-bromophenyl)-2-(3-cyclopentyloxy-4-methoxyphenyl) acetaldehyde, 7-Scheme-1. Robinson annulation of 7-Scheme-1 using methyl vinyl ketone with potassium hydroxide in ethanol provides 4-(4-bromophenyl)-4-(3-cyclopentyloxy-4-methoxyphenyl) cylohex-2-en-1-one, 8-Scheme-1. Suzuki coupling of 8-Scheme-1 with 2-(2-aminopyrimidin-5-yl)-4,4,5,5-tetramethyl-1,3-dioxaborolane [prepared from 2-amino-5-iodo pyrimidine by treatment with bis(pinacolato)diboron and 1,1'-bis(diphenylphosphino)ferrocene)dichloropalladium(II)] using tetrakis(triphenylphosphene)palladium (0) with sodium carbonate in toluene, provides 4-[4-(2-aminopyrimidin-5-yl)phenyl]-4-(3-cyclopentyloxy-4-methoxyphenyl) cyclohex-2-en-1-one, 9-Scheme-1. This is reduced first to 4-[4-(2-aminopyrimidin-5-yl)phenyl]-4-(3- cyclopentyloxy-4-methoxyphenyl)-cyclohexanone, 10-Scheme-1, by hydrogenation using catalytic palladium on carbon. Subsequent reduction of the ketone by sodium borohydride in methanol affords a cis- and trans-mixture of 4-[4-(2-aminopyrimidin-5-yl)phenyl]-4-(3-cyclopentyloxy-4-methoxyphenyl)-cyclohexanol, 11-Scheme-1. The cis- and trans-isomers can be separated by flash chromatography, then carried through the remainder of the synthesis independently. Independent Mitsunobu reaction of cis-Scheme-1 and trans-11-Scheme-1 using phthalimide with triphenylphosphine and diisopropyl azodicarboxylate, followed by hydrolysis with hydrazine monohydrate in ethanol, yields, respectively, trans- and cis-4-[4-(2-aminopyrimidin-5-yl)phenyl]-4-(3-cyclopentyloxy-4-methoxyphenyl)-cyclohexyl-1-amine, trans-12-Scheme-1 and cis-12-Scheme-1.

The following examples are given to illustrate the invention. They are not intended to limit the invention in any fashion.

EXAMPLES

Example 1

3-Cyclopentyloxy-4-methoxybenzaldehyde

A suspension of 3-hydroxy-4-methoxybenzaldehyde (30 g, 0.2 mol), cyclopentyl bromide (35.77 g, 0.24 mol) and potassium carbonate (38.6 g, 0.28 mol) in N,N-dimethylformamide (200 ml) was stirred vigorously for three days. Water (300 ml) was added and the mixture was extracted four times with ethyl acetate. The combined organic extract was washed three times with 10% aqueous sodium hydroxide solution, once with water, once with brine, dried (sodium sulfate) and evaporated to provide the title compound as a clear orange oil (36.47 g, 83%). $^1$H-NMR (400 MHz, CDCl$_3$): δ 9.84 (s, 1H), 7.43 (dd, 1H, J=8.3 Hz, 1.8 Hz), 7.39 (d, 1H, J=1.8 Hz), 6.96 (d, 1H, J=8.3 Hz), 4.86 (m, 1H), 3.93 (s, 3H), 2.0 (m, 2H), 1.8–1.95 (m, 4H), 1.63 (m, 2H)

Example 2

4'-Bromo-4-cyclopentyloxy-3-methoxybenzhydrol

To a solution of 1,4-dibromobenzene (25.72 g, 109 mmol) in dry tetrahydrofuran (50 ml) at isopropanolg/dry ice bath temperature under argon was added n-butyl lithium (43.6 ml of 2.5 M solution in hexane, 109 mmol) dropwise. This was stirred for one hour during which time a slurry formed. This slurry was added via cannula to a solution of 3-cyclopentoxy-4-methoxybenzaldehyde (20.0 g, 90.8 mmol) in dry THF (140 ml) at isopropanol/dry ice bath temperature. After one hour, the reaction was allowed to gradually warm to room temperature and stirred for an additional 4 h. The reaction was quenched with water then extracted three times with diethyl ether. The combined organic extract was washed successively with 1% hydrochloric acid, water, brine, then dried and evaporated. Purification by flash chromatography (silica gel, 17% ethyl acetate/83% hexane) provided the title compound as a pale white solid (36.78 g, 100% crude yield). MS (m/e): 359 [(M+1H$_2$O)$^+$]

Example 3

4'-Bromo-4-cyclopentyloxy-3-methoxybenzophenone

To a solution of 4'-bromo-4-cyclopentoxy-3-methoxybenzhydrol (10 g 0.5 mmol) in dichloromethane(50 ml), was added manganese (IV) oxide (24.0 g, 267 mmol). The mixture was stirred at the room temperature for two days then filtered through celite and the residue washed with dichloromethane. The filtrate was evaporated and the residue crystallized from ethanol to afford the title compound as a white solid (8.2 g, 83%). MS (m/e): 375 [(M+1)$^+$].

Example 4

2-(4-Bromophenyl)-2-(3-cyclopentyloxy-4-methoxyphenyl)acetaldehyde

Chloromethyltrimethylsilane (1.875 g, 15.37 mmol) in dry THF (45 ml) at −78° C. was treated with sec-butyllithium (13.0 ml of 1.3 M solution in cyclohexane, 16.88 mmol) followed by TMEDA (2.4 ml, 16.1 mmol). The mixture was stirred for 40 min, then warmed to −55° C. 4'-Bromo-4-cyclopentoxy-3-methoxybenzophenone (4.0 g, 10.6 mmol) in THF (20 ml) was added and the mixture stirred at −40° C. for 0.5 h. It was then warmed to room temperature gradually and stirred for an additional 18 h. The reaction was quenched with aqueous ammonium chloride solution and the resultant mixture extracted three times with ethyl acetate. The combined organic extract was washed with water then brine, dried (sodium sulfate) and evaporated. The residue was purified by flash chromatography (silica gel, 4% ethyl acetate/96% hexane). The resulting yellow oil was stirred in 50 ml of 20% trifluoroacetic acid in dichloromethane for one hour then washed three times with water, once with dilute sodium bicarbonate, twice with water, once with brine and dried (sodium sulfate). The solvent was evaporated to provide the title compound as a yellow oil (1.757 g, 42.5%). $^1$H-NMR (400 MHz, CDCl$_3$): δ 9.87 (s, 1H), 7.49 (d, 2H, J=8.4), 7.07 (d, 2H, J=8.4), 6.87 (d, 1H, J=8.2), 6.70 (dd, 1H, J=2.2, J=8.3), 6.68 (d, 1H, J=2.2).

Example 5

4-(4-Bromophenyl)-4-(3-cyclopentyloxy-4-methoxyphenyl)-2-cylohexen-1-one

To a solution of 2-(4-bromophenyl)-2-(3-cyclopentyloxy-4-methoxyphenyl) acetaldehyde (2.60 g, 6.7 mmol) in THF (10 ml) was added methyl vinyl ketone (670 ul, 8.4 mmol). The solution was stirred at −10° C. and 10% ethanolic potassium hydroxide (480 ul) was added slowly. After 0.5 h the reaction mixture was warmed to room temperature and stirred for additional 1 h. Water and ethyl acetate were added and the mixture was neutralized with 3N hydrochloric acid. The layers were separated and the aqueous layer washed twice with ethyl acetate. The combined organic extract was washed with water then brine, dried (sodium sulfate) and evaporated. Purification by flash chromatography (silica gel, 12% ethyl acetate/82% hexane) provided the title compound as a pale white waxy solid (1.39 g, 47%). MS (m/e): 441 [(M+1)$^+$], 443 [(M+3)$^+$].

Example 6

4-[4-(2-Aminopyrimidin-5-yl)phenyl]-4-(3-cyclopentyloxy-4-methoxyphenyl)-2-cyclohexen-1-one To a solution of 4-(4-bromophenyl)-4-(3-cyclopentyloxy-4-methoxyphenyl)-2-cylohexen-1-one (1.39 g, 3.17 mmol) in Toluene (50 ml) was added tetrakis(triphenylphosphine) palladium(0) (417 mg, 0.36 mmol), followed by 2-(2-aminopyrimidin-5-yl)-4,4,5,5-tetramethyl-1,3- dioxaborolane (2.02 g, 6.1 mmol, prepared as described in Tatsuo Ishiyama; Miki Murata and Norio Miyaura, J. Org. Chem. 1995, 60, 7508–7510), ethanol (8 ml) and 2M sodium carbonate (8 ml). The reaction mixture was stirred under argon at 80° C. for 18 h. Water was added and the mixture extracted three times with ethyl acetate, the combined organic extract was washed with water then brine, dried (sodium sulfate) and evaporated. Purification by flash chromatography (silica gel, 73% ethyl acetate/27% hexane) provided the title compound as a white solid (1.2 g, 83% crude yield). MS (m/e): 456 [(M+1)$^+$].

Example 7

4-[4-(2-Aminopyrimidin-5-yl)phenyl]-4-(3-cyclopentyloxy-4-methoxyphenyl)-cyclohexanone A slurry of 4-[4-(2-aminopyrimidin-5-yl)phenyl]-4-(3-cyclopentyloxy-4-methoxyphenyl)-2-cyclohexen-1-one (1.2 g, 2.63 mmol) in ethyl acetate (20 ml) with palladium on activated carbon (360 mg, 30% w/w) was stirred under hydrogen at atmospheric pressure for three days then filtered and the residue washed with dichloromethane. The combined organic solution was evaporated to afford the title compound as a gray solid (1.05 g, 88% crude yield). $^1$H-NMR (400 MHz, CDCl$_3$): δ 8.51 (s, 2H), 7.44 (d, 2H, J=8.4), 7.38 (d, 2H, J=8.4), 6.89 (dd, 1H, J=8.4, J=2.2), 6.84 (d, 1H, J=8.4), 6.83 (d, 1H, J=2.2), 5.21 (s, 2H), 4.69 (m, 1H), 3.83(s, 3H), 2.64 (m, 4H), 2.48 (m, 4H). 1.81 (m, 6H), 1.57 (m, 2H).

Example 8

4-[4-(2-Aminopyrimidin-5-yl)phenyl]-4-(3-cyclopentyloxy-4-methoxyphenyl)-cyclohexanol Sodium borohydride (86.6 mg, 2.29 mmol) was added to a slurry of 4-[4-(2-aminopyrimidin-5-yl)phenyl]-4-(3-cyclopentyloxy-4-methoxyphenyl)-cyclohexanone (1.05 g, 2.29 mmol) in methanol (50 ml) and tetrahydrofuran (12.5 ml). The mixture was stirred for 1.5 h (the slurry became a clear solution after 10 min). Acetone was added to destroy the excess sodium borohydride and all the solvent was removed. The residue was evaporated twice from methanol then dissolved in ethyl acetate and washed with water then brine and dried (sodium sulfate). Evaporation of solvent followed by purification by flash chromatography (silica gel, 5% methanol/95% dichloromethane) provided cis-4-[4-(2-aminopyrimidin-5-yl)phenyl]-4-(3-cyclopentyloxy-4-methoxyphenyl)-cyclohexanol as a white solid (485 mg, 46%). MS (m/e): 460 (M+1)$^+$; and trans-4-[4-(2-aminopyrimidin-5-yl)phenyl]-4-(3-cyclopentyloxy-4-methoxyphenyl)-cyclohexanol as a white solid (458 mg, 43%), MS (m/e): 460 (M+1)$^+$.

Example 9

Trans-4-[4-(2-aminopyrimidin-5-yl)phenyl]-4-(3-cyclopentyloxy-4-methoxyphenyl)-cyclohexyl-1-amine To a solution of cis-4-[4-(2-aminopyrimidin-5-yl)phenyl]-4-(3-cyclopentyloxy-4-methoxyphenyl)-cyclohexanol (462 mg, 1.01 mmol) in THF (15 ml) was added triphenylphosphine (1.318 g, 5.58 mmol), phthalimide (740 mg, 5.58 mmol) and diisopropyl azodicarboxylate (1.0 ml, 5.58 mmol). This was stirred for 18 h then solvent was removed. The residue was purified by flash chromatography (silica gel, 3% methanol/97% dichloromethane) and the resulting crude trans-4-[4-(2-aminopyrimidin-5-yl)phenyl]-4-(3-cyclopentyloxy-4-methoxyphenyl)-1-phthalimido-cyclohexane [MS(m/e):589 (M$^+$+1)] was used without farther purification.

To a solution of trans-4-[4-(2-aminopyrimidin-5-yl) phenyl]-4-(3-cyclopentyloxy-4-methoxyphenyl)-1-phthalimido-cyclohexane (crude product from previous step) in ethanol (20 ml) was added hydrazine monohydrate (2.0 ml) and the resulting solution was heated to reflux for 4 h. The solvent was removed and the residue dissolved in ethyl acetate then washed with 3N hydrochloric acid three times. The combined aqueous extract was washed with ethyl acetate once then neutralized with 10% aqueous sodium hydroxide solution and extracted four times with ethyl acetate. The combined organic extract was washed with water, brine then dried (sodium sulfate) and solvent removed in vacuo. Purification by flash chromatography (silica gel, 5% methanol/94% dichlromethane/1% ammonium hydroxide) followed by preparative HPLC provided the title compound as a white solid (120 mg, 26%). MS (m/e): 459 [(M+1)$^+$].

Example 10

Cis-4-[4-(2-Aminopyrimidin-5-yl)phenyl]-4-(3-cyclopentyloxy-4-methoxyphenyl)-cyclohexyl-1-amine The title compound was prepared following the procedure in (9) except substituting trans-4-[4-(2-amninopyrimidin-5-yl)phenyl]-4-(3-cyclopentyloxy-4-methoxyphenyl)-cyclohexanol for cis-4-[4-(2-aminopyrimidin-5-yl)phenyl]-4-(3-cyclopentyloxy-4-methoxyphenyl)-cyclohexanol. Purification by flash chromatography (silica gel, 5% methanol/94% dichlromethane/1% ammonium hydroxide) followed by preparative HPLC provided cis-4-[4-(2-aminopyrimidin-5-yl)phenyl]-4-(3-cyclopentyloxy-4-methoxyphenyl)-cyclohexyl-1-amine as a white solid (120 mg, 41%). MS (m/e): 459 [(M+1)$^+$].

UTILITY EXAMPLES

Example A

Inhibitory Effect of Compounds of Formula (I) and (II) on In Vitro TNF Production by Human Monocytes The inhibitory effect of compounds of Formula (I) and (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I) and (II). The protocol used in these models is described in Badger et al., EPO published Application 0 411 754 A2, Feb. 6, 1991, and in Hanna. WO 90/15534, Dec. 27, 1990.

The compound of Example 1 herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) and (II) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50's}$ in the nanomolar to $\mu M$ range for compounds of the workings examples described herein for Formula (I) and (II) have been demonstrated.

What is claimed is:

1. A compound of Formula(I)

(I)

wherein:
  $R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties unsubstituted or substituted with one or more halogens;
  m is 0 to 2;
  n is 1 to 4;
  r is 0 to 6;
  $R_4$ and $R_5$ are independently selected hydrogen or $C_{1-2}$ alkyl;
  $R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;
  provided that:
    a) when $R_6$ is hydroxyl, then m is 2; or
    b) when $R_6$ is hydroxyl, then r is 2 to 6; or
    c) when $R_6$ is 2-tetrahydropyranyl, 2-tetrahydrothiopyranyl, 2-tetrahydrofuranyl, or 2-tetrahydrothienyl, then m is 1 or 2; or
    d) when $R_6$ is 2-tetrahydropyranyl, 2-tetrahydrothiopyranyl, 2-tetrahydrofuranyl,or 2-tetrahydrothienyl, then r is 1 to 6;
    e) when n is 1 and m is 0, then $R_6$ is other than H in $-(CR_4R_5)_nO(CR_4R_5)_mR_6$;
  X is $YR_2$, fluorine, $NR_4R_5$, or formyl amine;
  Y is O or $S(O)_{m'}$,
  m' is 0, 1, or 2;
  $X_2$ is O or $NR_8$;
  $X_4$ is H, $R_9$, $OR_8$, CN, $C(O)R_8$, $C(O)OR_8$, $C(O)NR_8R_8$, or $NR_8R_8$;
  $R_2$ is independently selected from $-CH_3$ or $-CH_2CH_3$ optionally substituted by 1 or more halogens;
  s is 0 to 4;

Ar is phenyl unsubstituted or substitued by $R_7$;
Z is $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2(SR_9)$, $NR_{10}C(NR_{10})NR_{10}R_{14}$, $NR_{10}C(O)C(O)NR_{10}R_{14}$, or $NR_{10}C(O)C(O)OR_{14}$;
Y' is O or S;
  $R_7$ is $-(CR_4R_5)_qR_{12}$ or $C_{1-6}$ alkyl wherein: the $R_{12}$ or $C_{1-6}$ alkyl group is unsubstituted or substituted one or more times by methyl or ethyl unsubstituted or substituted by 1–3 fluorines; —F; —Br; —Cl; $-NO_2$; $-NR_{10}R_{11}$; $-C(O)R_8$; $-CO_2R_8$; $-O(CH_2)_{2-4}OR_8$; $-O(CH_2)_qR_8$; —CN; $-C(O)NR_{10}R_{11}$; $-O(CH_2)_qC(O)NR_{10}R_{11}$; $-O(CH_2)_qC(O)_9$; $-NR_{10}C(O)NR_{10}R_{11}$; $-NR_{10}C(O)R_{11}$; $-NR_{10}C(O)OR_9$; $-NR_{10}C(O)R_{13}$; $-C(NR_{10})NR_{10}R_{11}$; $-C(NCN)NR_{10}R_{11}$; $-C(NCN)SR_9$; $-NR_{10}C(NCN)SR_9$; $-NR_{10}C(NCN)NR_{10}R_{11}$; $-NR_{10}S(O)_2R_9$; $-S(O)_{m'}R_9$; $-NR_{10}C(O)C(O)NR_{10}R_{11}$; $-NR_{10}C(O)C(O)R_{10}$; or $R_{13}$;
  q is 0, 1, or 2;
  $R_{12}$ is $R_{13}$, $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$; or $C_3-C_7$ cycloalkyl, or (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, or phenyl, wherein each of (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, or phenyl may be substituted by $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$;
  $R_8$ is independently selected from hydrogen or $R_9$;
  $R_9$ is $C_{1-4}$ alkyl optionally substituted by one to three fluorines;
  $R_{10}$ is $OR_8$ or $R_{11}$;
  $R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;
  $R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_qNR_8R_{14}$ or $S(O)_qR_7$ where q is 0, 1 or 2;

provided that:
(f) $R_7$ is not $C_{1-4}$ alkyl unsubstituted or substituted by one to three fluorines;

or the pharmaceutically acceptable salts thereof.

2. A compound according to claim 1 wherein $R_1$ is —$CH_2$-cyclopropyl, —$CH_2$—$C_{5-6}$ cycloalkyl, —$C_{4-6}$ cycloalkyl unsubstituted or substituted by OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, and X is $YR_2$.

3. A compound according to claim 1 wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl.

4. A compound according to claim 1 which is cis-4-[4-(2-aminopyrimidin-5-yl)phenyl]-4-(3-cyclopentyloxy-4-methoxyphenyl)-cyclohexanol;

trans-4-[4-(2-aminopyrimidin-5-yl)phenyl]-4-(3-cyclopentyloxy-4-methoxyphenyl)-cyclohexyl-1-amine;

cis-4-[4-(2-Aminopyrimidin-5-yl)phenyl]-4-(3-cyclopentyloxy-4-methoxyphenyl)-cyclohexyl-1-amine; and trans-4-[4-(2-Aminopyrimidin-5-yl)phenyl]-4-(3-cyclopentyloxy-4-methoxyphenyl)-cyclohexyl-1-amine.

5. A compound of Formula (II)

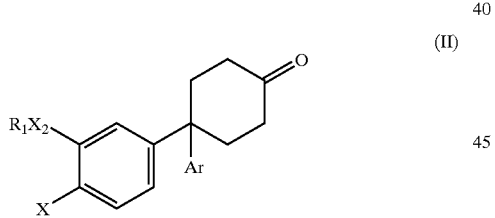

(II)

wherein:
$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties unsubstituted or substituted with one or more halogens;

m is 0 to 2;
n is 1 to 4;
r is 0 to 6;
$R_4$ and $R_5$ are independently selected hydrogen or $C_{1-2}$ alkyl;
$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl or heterocyclic moiety is unsubstituted or substituted by 1 to 3 methyl groups, one ethyl group, or an hydroxyl group;

provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl,or 2-tetrahydrothienyl, then r is 1 to 6;
e) when n is 1 and m is 0, then $R_6$ is other than H in —$(CR_4R_5)_nO(CR_4R_5)_mR_6$;

X is $YR_2$, fluorine, $NR_4R_5$, or formyl amine;
Y is O or $S(O)_{m'}$;
m' is 0, 1, or 2;
$X_2$ is O or $NR_8$;
$X_4$ is H, $R_9$, $OR_8$, CN, $C(O)R_8$, $C(O)OR_8$, $C(O)NR_8R_8$, or $NR_8R_8$;
$R_2$ is independently selected from —$CH_3$ or —$CH_2CH_3$ optionally substituted by 1 or more halogens;
s is 0 to 4;
Ar is phenyl unsubstituted or substitued by $R_7$;
$R_7$ is —$(CR_4R_5)_qR_{12}$ or $C_{1-6}$ alkyl wherein: the $R_{12}$ or $C_{1-6}$ alkyl group is unsubstituted or substituted one or more times by methyl or ethyl unsubstituted or substituted by 1–3 fluorines; —F; —Br; —Cl; —$NO_2$; —$NR_{10}R_{11}$; —$C(O)R_8$; —$CO_2R_8$; —$O(CH_2)_{2-4}OR_8$; —$O(CH_2)_qR_8$; —CN; —$C(O)NR_{10}R_{11}$; —$O(CH_2)_qC(O)NR_{10}R_{11}$; —$O(CH_2)_qC(O)R_9$; —$NR_{10}C(O)NR_{10}R_{11}$; —$NR_{10}C(O)R_{11}$; —$NR_{10}C(O)OR_9$; —$NR_{10}C(O)R_{13}$; —$C(NR_{10})NR_{10}R_{11}$; —$C(NCN)NR_{10}R_{11}$; —$C(NCN)SR_9$; —$NR_{10}C(NCN)SR_9$; —$NR_{10}C(NCN)NR_{10}R_{11}$; —$NR_{10}S(O)_2R_9$; —$S(O)_{m'}R_9$; —$NR_{10}C(O)C(O)NR_{10}R_{11}$; —$NR_{10}C(O)C(O)R_{10}$; or $R_{13}$;

q is 0, 1, or 2;
$R_{12}$ is $R_{13}$, $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$, or $NR_{10}C(O)C(O)OR_{14}$; or $C_3$–$C_7$ cycloalkyl, or (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, or phenyl, wherein each of (2-, 3- or 4-pyridyl), pyrimidinyl, pyrazolyl, (1- or 2-imidazolyl), pyrrolyl, piperazinyl, piperidinyl, morpholinyl, furanyl, (2- or 3-thienyl), quinolinyl, naphthyl, or phenyl may be substituted by $OR_{14}$, $OR_{15}$, $SR_{14}$, $S(O)_{m'}R_7$, $S(O)_2NR_{10}R_{14}$, $NR_{10}R_{14}$, $NR_{14}C(O)R_9$, $NR_{10}C(Y')R_{14}$, $NR_{10}C(O)OR_7$, $NR_{10}C(Y')NR_{10}R_{14}$, $NR_{10}S(O)_2NR_{10}R_{14}$, $NR_{10}C(NCN)NR_{10}R_{14}$, $NR_{10}S(O)_2R_7$, $NR_{10}C(CR_4NO_2)NR_{10}R_{14}$, $NR_{10}C(NCN)SR_9$, $NR_{10}C(CR_4NO_2)SR_9$, $NR_{10}C(NR_{10})NR_{10}R_{14}$, $NR_{10}C(O)C(O)NR_{10}R_{14}$,or $NR_{10}C(O)C(O)OR_{14}$;

$R_8$ is independently selected from hydrogen or $R_9$;
$R_9$ is $C_{1-4}$ alkyl optionally substituted by one to three fluorines;
$R_{10}$ is $OR_8$ or $R_{11}$;
$R_{11}$ is hydrogen, or $C_{1-4}$ alkyl unsubstituted or substituted by one to three fluorines; or when $R_{10}$ and $R_{11}$ are as $NR_{10}R_{11}$ they may together with the nitrogen form a 5 to 7 membered ring comprised of carbon or carbon and one or more additional heteroatoms selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups unsubstituted or substituted on the methyl with 1 to 3 fluoro atoms;

$R_{14}$ is hydrogen or $R_7$; or when $R_8$ and $R_{14}$ are as $NR_8R_{14}$ they may together with the nitrogen form a 5 to 7 membered ring comprised of carbon or carbon and one or more additional heteroatoms selected from O, N, or S;

$R_{15}$ is $C(O)R_{14}$, $C(O)NR_8R_{14}$, $S(O)_qNR_8R_{14}$ or $S(O)_qR_7$ where q is 0, 1 or 2;

provided that:
(f) $R_7$ is not $C_{1-4}$ alkyl unsubstituted or substituted by one to three fluorines;
or the pharmaceutically acceptable salts thereof.

6. A compound according to claim 5 wherein A compound according to claim 1 wherein $R_1$ is —$CH_2$-cyclopropyl, —$CH_2$—$C_{5-6}$ cycloalkyl, —$C_{4-6}$ cycloalkyl unsubstituted or substituted by OH, tetrahydrofuran-3-yl, (3- or 4-cyclopentenyl), benzyl or —$C_{1-2}$ alkyl unsubstituted or substituted by 1 or more fluorines, and —$(CH_2)_{2-4}$ OH; $R_2$ is methyl or fluoro-substituted alkyl, and X is $YR_2$.

7. A compound according to claim 5 wherein A compound according to claim 1 or 2 wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl.

8. A compound according to claim 5 which is 4-[4-(2-aminopyrimidin-5-yl)phenyl]-4-(3-cyclopentyloxy-4-methoxyphenyl)-cyclohexanone.

9. A pharamceutical composition comprising a compound of claim 1 and a pharamceutically acceptable excipient.

10. A pharmaceutical composition comprising a compound of claim 5 and a pharmaceutically acceptable excipient.

11. A method for treating an inflammatory disease which method comprises administering a compound according to claim 1 in combination with a pharamceutically acceptable excipient to a patient in need thereof.

* * * * *